(12) United States Patent  (10) Patent No.: US 6,681,640 B2
Canumalla  (45) Date of Patent: Jan. 27, 2004

(54) TEST FIXTURE AND METHOD (75) Inventor: Sridhar Canumalla, Flower Mound, TX (US)

(73) Assignee: Nokia Corporation, Espoo (FI)

( * ) Notice: Subject to any disclaimer, the term of this patent is extended or adjusted under 35 U.S.C. 154(b) by 0 days.

(21) Appl. No.: 10/085,265

(22) Filed: Feb. 28, 2002

(65) Prior Publication Data

US 2003/0159520 A1 Aug. 28, 2003

(51) Int. Cl.[7] ................................................. G01N 3/02
(52) U.S. Cl. ....................................................... 73/856
(58) Field of Search ......................... 73/760, 781, 788, 73/789, 815, 826, 841, 790, 796, 818, 856

(56) References Cited

U.S. PATENT DOCUMENTS

| 3,443,423 | A | * | 5/1969 | R. E. Lou Ma | 73/821 |
| 3,693,421 | A | * | 9/1972 | Karper et al. | 73/843 |
| 4,018,080 | A | * | 4/1977 | Fletcher et al. | 73/816 |
| 5,305,634 | A | * | 4/1994 | Suga et al. | 73/856 |
| 5,677,494 | A | * | 10/1997 | Keener et al. | 73/760 |
| 5,811,686 | A | * | 9/1998 | Lavoie et al. | 73/821 |
| 6,234,029 | B1 | * | 5/2001 | Liang et al. | 73/850 |

\* cited by examiner

Primary Examiner—Max Noori
(74) Attorney, Agent, or Firm—Steven Shaw (57) ABSTRACT A test fixture and method for mechanical testing of production samples of semiconductor chips that have been packaged and mounted on a printed circuit board. The sample is isolated and attached to a loading arm using an adhesive. The test fixture includes at least four plates disposed in a spaced-apart relationship along a testing axis. At least six rods are used to maintain this alignment. A first rod set of at least three rods is fixed in a first direction along the testing axis. The first rod set extends parallel to the testing axis through openings formed in a second plate to the third plate, to which the first rod set is fixed in at least a second direction along the testing axis, the second direction being opposite to the first direction. Similarly, a second set of at least three rods are fixed in the first direction to a second plate, extend along the testing axis through openings formed in the third plate, and are fixed in a second direction to the fourth plate. The loading arm bearing the specimen is fixed between the second and third plates for shear testing and between the second and fourth for tensile testing.

17 Claims, 11 Drawing Sheets

Upper Arm

Lower Arm

Thin Groove For
Alignment

TEST FIXTURE AND METHOD

The present invention relates generally to the field of mechanical-strength test fixtures, and more specifically to a test fixture and method for assessment of joint strength of a multiple interconnection microelectronic component mounted on a printed circuit board or other substrate.

BACKGROUND OF THE INVENTION

As electrical devices become both more capable and more popular, the market pressure to reduce costs while providing ever-more-reliable performance increases. This applies not only to computers and conventional cellular phones, but to devices such as personal digital assistants (PDAs), handheld electronic games, digital pagers, and Web phones as well. These devices are expected to provide reliable service notwithstanding the sophisticated technology they embody and their mobile nature. In addition, the instruments themselves are getting smaller. This is largely due to fast-paced technological innovation producing miniature electrical components, but also has the effect of forcing designers and manufacturers to abandon thick, sturdy enclosures in favor of more light-weight construction.

Notwithstanding the diminished ability of today's electronic devices to withstand shock and bending stresses when compared to their bulkier predecessors, the size itself may contribute to rougher treatment. For example, custom carrying cases and automobile mounting for mobile telephones are no longer de rigueur; modern telephones may be simply hung from a belt, or stuffed into a pocket, purse, or briefcase. PDAs and even palm-top computers are subject to similar handling. And being smaller, they are sometimes easier to mishandle. But modern devices are expected to put up with such treatment.

What must actually withstand this somewhat rough treatment, of course, are the device's internal components. Along with ways to make them smaller, scientists and engineers continually look for ways to improve the ability of electronic components to withstand the rigors of contemporary usage. As new strategies are tried, of course, new ways are developed to test their success at increasing mounted component's shock-withstanding performance. As the present invention is directed to a fixture for performing such testing, a brief introduction to the components being tested will now be provided.

With the invention of the integrated circuit and the development of semiconductor technology, packaged chips replaced the tubes, wires, and mechanical switches of an earlier generation. A "chip" is a small piece of semiconducting material, such as silicon that has been "doped". Doping involves treating selected areas of the silicon with a doping agent such as boron, phosphorous, or erbium. These agents alter how the silicon will act electrically in the presence of an applied voltage or other stimulus. (Other types of treatment are used, as well.) Selective treatment of the silicon surface is often done through a process known as photolithography. In photolithography, a silicon wafer is covered with photoresist. A finely-tuned opto-mechanical device called a stepper exposes certain areas on the wafer to, for example, ultraviolet light, which cause some of the photoresist to harden (or soften) so that the selected portions may be washed away by an appropriate solvent. The partially exposed surface is then subject to doping, etching, or filling with a conductive material, and the remaining photoresist is removed. The process may be repeated any number of times to build the desired electrical components. The dozens of identical integrated circuits thus formed on the finished wafer surface are then separated from each other and encapsulated in plastic packages. These packages protect the chip and permit it to be transported and installed. Protruding through the package will necessarily be some form of conductor that connects the integrated circuit on the chip to the remainder of the electrical device in which it is to be used.

Component-manufacturing processes such as the one described above have resulted in smaller and smaller components that nevertheless offer greatly increased capabilities. The same is true for standard electrical components such as non-chip-integrated resistors and capacitors. These smaller components do not require study chasses to hold them in place, but can simply be mounted on a PCB made of non-conducting material and the whole assembly enclosed in a lightweight plastic container—which also makes the device more portable. Although well-packaged, electronic components may nevertheless include many metallic connections to the printed circuit board (PCB). Board-mounted electrical components are used in a great many applications.

There are, generally speaking, three types of methods in common use for mounting electrical components to PCBs. First, the PCB may form an opening through which a component lead is inserted. A conductive trace on the PCB makes contact with the lead, which his usually soldered into place to ensure connectivity and to hold the component in place. Another component lead is attached through another opening in similar fashion. A single component may have only two or more than a dozen leads. In a second matter of attaching, the component has a plurality of relatively short leads, often called pins. The pins are inserted into sockets that are part of a previously installed terminal block. Finally, the electrical component may simply be attached to corresponding leads or traces present on the circuit-board surface. Such devices are often called surface-mount components and, since they use no through-hole or socket, must rely exclusively on the solder (or similar) joint to hold the component in place and to maintain each connection.

As previously mentioned, designers may wish to test the integrity of connections such as these to determine whether they are adequate and to plan for future improvements. As with many other mass-produced items, these devices are often tested destructively. That is, some adverse force or environmental condition, or both, is applied until the device fails. The device itself is thereafter unusable, unless repaired, but the critical condition causing failure is measured and recorded for comparison with other designs. Naturally, the accuracy of such tests is expected to improve as the number of sample tests increases.

Given the difficulties inherent in mechanically testing microcomponents, such testing frequently is performed on larger, isolated laboratory samples. For example, to estimate the shear strength of the mounting of an area-array mounted chip (See, e.g., FIGS. 1C and 2C), a single solder ball might be tested. The results are then extrapolated to approximate the expected strength of an entire installed. This nevertheless puts the designer at a disadvantage because the use of a single laboratory-sample solder ball may not very closely compare to an actual production-line installed chip.

At the other end of the spectrum, testing may be accomplished using the entire instrument, which also may be subject to various environmental conditions or simply dropped. When failure does occur, that is, the device becomes inoperable, the various components may be visually inspected or electronically tested to determine which ones contributed to the failure.

Note that as used herein, the terms electronic "device", "instrument", and the like will be used interchangeably to refer to manufactured products containing one or more electrical "components" or "micro-components" to perform the designed function. "Mounting" simply refers to the manner in which the component is fixed within the device. In the context of the present invention, this will often, but not necessarily, be done using a soldered connection. In short, the present invention is not limited in how it can be used, or on what specific components, save by whether they are of a construction that can be in some way placed into the fixture for testing.

Obviously, both the single solder ball test and complete-device test are useful, but unsatisfactory for determining the strength of a single mounted component. And conventional testing equipment is typically not suited to testing mounted components. Needed is a testing fixture capable of performing accurate strength tests on mounted components that closely resemble those used in the actual electronic device. The present invention provides just such a device, and a method of using it.

SUMMARY OF THE INVENTION

The present invention is directed to a test-fixture for testing mounted electrical components and to a method for using the fixture. In one aspect, the present invention is a test fixture including at least four plates stacked in a spaced relationship along a test-force axis; alternate plates being connected to one another via a plurality of alignment rods. The interior plates form openings so that the alignment rods connecting adjacent plates may pass through. Each of two loading arms are fixed to facing surfaces of two adjacent plates; the loading arms being positioned so as to apply a testing force to a specimen positioned between them when a force is applied by an external means to the outer plates.

In another aspect, the present invention is a method of testing mounted electrical components, including the steps of attaching the components to at least one of two loading arms, fixing the loading arms to adjacent plates in a test fixture having four plates, alternating plates being connected to each other by alignment rods. The method further includes the step of applying a force to the test fixture causing the loading arms to apply a force to the specimen.

BRIEF DESCRIPTION OF THE DRAWINGS

FIG. 5 is a detailed illustration of loading arms used for shear testing according to one embodiment of the present invention, and includes:

FIG. 7 is a detailed illustration of the test-fixture shear-test loading arms according to an alternate embodiment of the present invention, and includes FIG. 7A, a side view of both arms in testing position; FIG. 7C, a front view of the upper loading arm.

FIG. 8 is a detailed illustration of the test-fixture shear-test loading arms according to an alternate embodiment of the present invention, and includes FIG. 8A, a side view of both arms in testing position; FIG. 8B, a front view of the lower loading arm; FIG. 8C, a front view of the upper loading arm; FIG. 8D, a partial close-up side view of the upper loading arm and the lower loading arm capturing a specimen for shear testing; and FIG. 8E, a sectional view illustrating the dove-tail and groove, taken along line X—X shown in FIG. 8A;

FIG. 10 is a detailed illustration of the loading arms for pull testing according to an embodiment of the present invention and includes FIG. 10A, an isometric view of the lower loading arm; FIG. 10B, a top view of the lower loading arm; FIG. 10C, a side view of the lower loading arm.

DETAILED DESCRIPTION

Figure 1A:
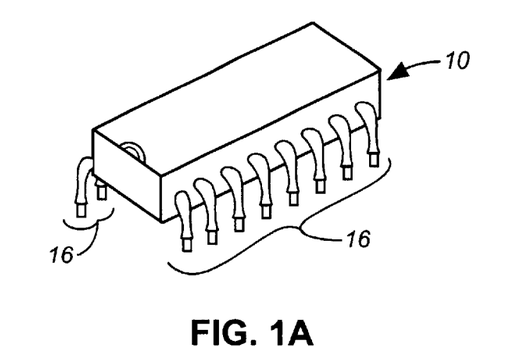
FIG. 1A is an illustration of a typical dual-in-line packaged semiconductor chip.
Figure 1B:
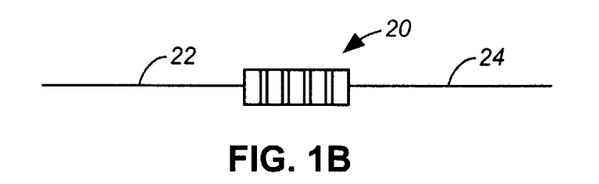
FIG. 1B is an illustration of a resistor.
Figure 1C:
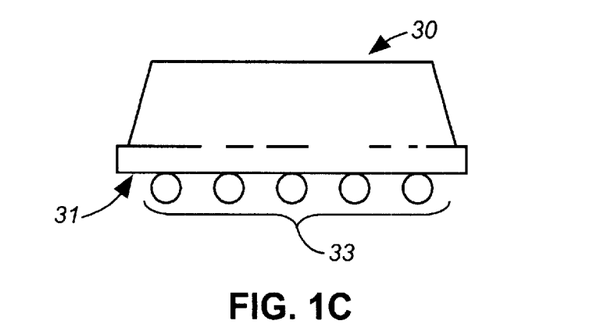
FIG. 1C is an illustration of a typical area-array packaged semiconductor chip.
Figure 1D:
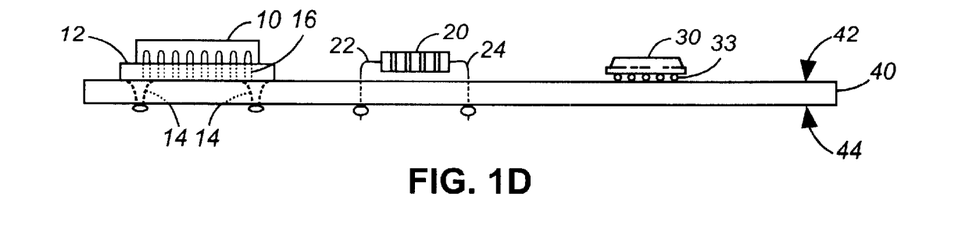
FIG. 1D is an illustration of the electronic devices shown in FIGS. 1A–1C, mounted onto a printed circuit board (PCB)

FIGS. 1A–1C illustrate typical mountable electronic components; FIG. 1A shows a dual-in-line package (DIP) chip 10; FIG. 1B depicts a resistor 20; and FIG. 1C shows an area-array chip 30. In each of these devices, the features used to mount the device are also the electrical leads. The actual electronic component is enclosed in a package through which the leads extend, providing the conductive path from the component to the circuit of which it is a part. Chip 10 has sixteen pins (eight on each side), collectively enumerated as pins 16. When mounted, pins 16 will be received into openings formed in socket 12 (shown in FIG. 1D), and will generally fit tightly enough so that chip 10 will not easily be dislodged. FIG. 1D depicts a printed circuit board (PCB) 40 onto which electronic components may be mounted. In the case of chip 10, it may actually be the socket 12 that is mounted to PCB 40, in FIG. 1D by passing mounting pegs 14 through corresponding openings formed in PCB 40 and soldering them in place. Resistor 20 is similarly attached by leads 22 and 24, which pass through PCB 40, and are soldered into place. The excess portion of leads 22 and 24 may be trimmed. Area-array chip 30 is mounted somewhat differently. Sometimes referred to as a surface mounting, small solder balls 33 are affixed to the leads (not shown) on the underside 31 of chip 30. Although five balls 33 are shown, there may be dozens. The chip 30 is mounted by heating contacts (not shown) on the upper surface 42 of PCB 40 sufficiently so that when area-array chip 30 is set into place, the solder balls 33 melt sufficiently to form a permanent contact. Thin electrical conductors, sometimes called traces (not shown), run along the upper surface 42 or lower surface 44 of PCB 40, or between them through appropriately placed openings. The traces, of course, also connect to the mounting of the electronic components. It is these connections, in general, that will be tested using the apparatus and method of the present invention.

Note that the devices shown in FIGS. 1A–1D are exemplary, not limiting, and there are literally hundreds of such devices and many ways to mount them on a PCB such as PCB 40.

Further background will now be provided by showing a PCB mounted in an exemplary electronic device, here a mobile telephone.

Figure 2A:
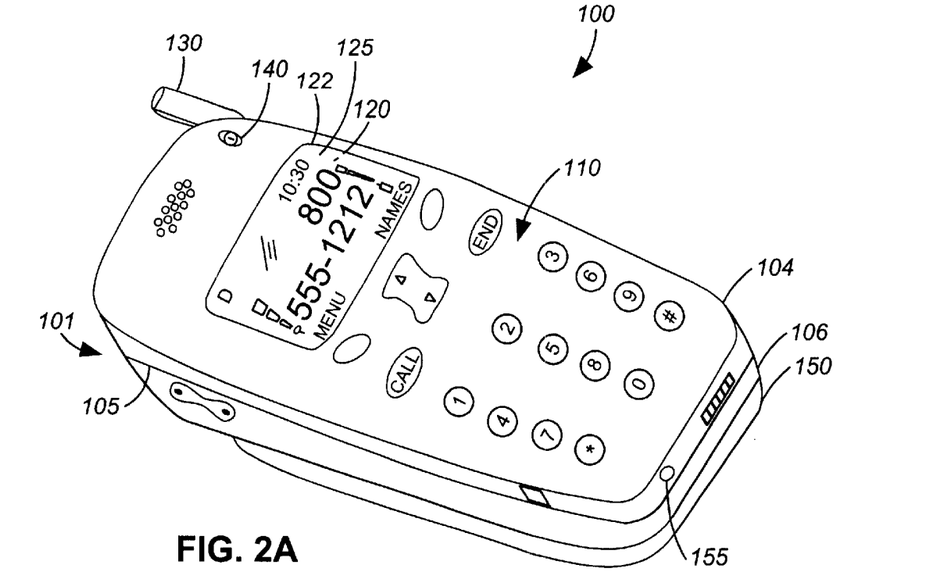
FIG. 2A is an illustration of a typical mobile telephone having internal components mounted on a printed circuit board (PCB) that may be tested using the test fixture and method according to the present invention.

One application where the present invention is expected to be used to great advantage is in testing mounted components as used in mobile telephones. FIG. 2A shows a conventional mobile telephone 100. There are many variations of this basic instrument now in use, but many of the components in each of them are similar, they will all be subject to testing using the test fixture and method of the present invention. Mobile telephone 100 includes keypad 110, which is a user interface for entering telephone numbers and other data, programming various mobile-phone functions, and establishing and disconnecting telephone calls. The user may read and review the dialed number, or perhaps the identity of a user associated with an incoming call, or liquid crystal display (LCD) 120. LCD 120 is visible from the exterior through opening 122 in front cover 104 and transparent protective cover 125. Antenna 130 is provided to facilitate radio transmission and reception, though in other phones the antenna may be completely internal and thus not visible from the outside. A power switch 140 turns the unit on and off. The power source during mobile operation is a battery 150, which on the illustrated telephone is removably attached to the rear of the unit. In other designs, the battery may simply be retained inside the enclosure 101 with the rest of the phone's internal components. Power for recharging the attached battery is supplied through an AC adaptor (not shown) that can be plugged into power port 155.

Figure 2B:
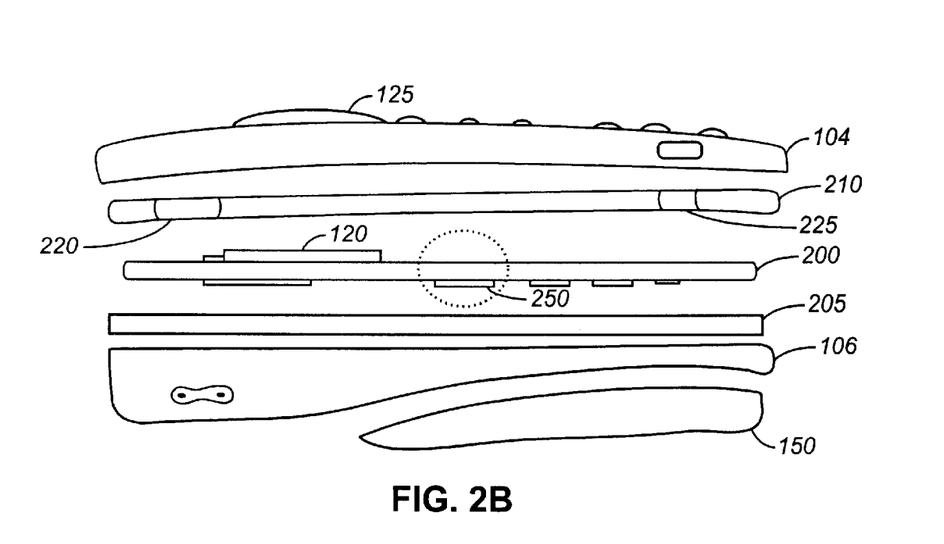
FIG. 2B is an exploded view of the mobile phone of FIG. 2A, revealing the PCB.

The internal components (not shown in FIG. 2A) of mobile telephone 100 are securely retained in the enclosure 101, which normally has two (or more) cover portions, here front cover 104 and back cover 106 which meet at enclosure joint 105. FIG. 2B is an exploded view of the mobile telephone 100 of FIG. 2A. In this view, the front cover 104 and back cover 106 are separated to reveal a printed circuit board (PCB) 200, upon which are mounted most of the internal electronic circuitry of telephone 100. BGA-mounted chip 250 an area-array device is called out as an example. When the phone is assembled, PCB 200 is captured between the face 210 and chassis body 205, and this internal assembly is in turn captured between front cover 104 and back cover 106. Other internal components such as a speaker 220, a microphone 225, and the LCD 120 are likewise enclosed.

Figure 2C:
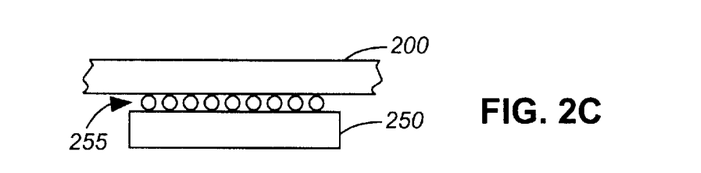
FIG. 2C is a partial close-up view of the PCB visible in FIG. 2B, showing in detail an exemplary mounted electrical component.

FIG. 2C is a side view of exemplary BGA-mounted chip 250 as it is attached to PCB 200 (only a portion of which is shown in FIG. 2B) by solder balls 255. Note that although only nine solder balls 255 are shown, there may be—and usually are—many more. In a preferred embodiment, the test apparatus of the present invention is used to test mountings similar to the one securing chip 250 to the PCB 200.

Testing Protocol—General

Testing using the apparatus of the present invention will include both shear and tensile (pull) testing. Preferably, the same test apparatus is used for both, with alteration being made to the loading arms to accommodate the needs of each type of test. As mentioned previously, one of the advantages afforded by the apparatus of the present invention is the ability to test production samples rather than laboratory versions created solely for the purposes of testing. Laboratory samples may, of course, be tested as well. Note also that the sample tested may be from a device that is not new, but rather has been in storage or use for some time. Preconditioning may also be employed, that is, subjecting the specimen (as prepared for testing or while still installed in the mobile device) to a range of tests or environmental conditions prior to testing using the fixture of the present invention. The actual test may also be performed under varying environmental conditions as well (for example, high or low temperature, radiation, or humidity).

The production sample will typically take the form of populated PCB 200 shown in FIG. 2B. The specimen to be tested (for example, chip 250) is isolated and PCB section containing it carefully cut away. Any cutting or trimming method may be used, bearing in mind that the integrity of the subject connection must not be compromised, or altered from its original condition. As populated circuit boards may have other electrical components positioned very near each other, non-tested components may have to be removed to avoid their influence on the accuracy of the test results. Alternately, the PCB 200 may be constructed in the normal fashion, but including only one or more relatively spaced apart components that can be separated and tested. In this case, care must be taken not to omit construction elements and operations that may, although concerned with separate components, nevertheless affect the mounting of the component to be tested. In other words, to obtain a valid "production sample", the specimen must have undergone the normal production sequence, at least insofar as any sequence step has the potential to disturb the specimen.

Once a satisfactory specimen has been isolated, it is attached to the appropriate loading arm or arms; typically using an adhesive. There are many adhesives that may be used for this purpose, though of course for accurate testing the bond should be significantly stronger than the mounting being tested. Desirable configurations for attaching the specimen to the test apparatus of the present invention are described below. Once installed on the loading arm, proper mounting is verified, if desired, and then the specimen-bearing loading arm is installed in the test fixture itself.

The test fixture is then installed onto the load-producing machine, although note that this may actually be done either before or after the specimen has been installed. Any satisfactory testing machine may be used, bearing in mind that anticipated testing loads and deformation will be relatively small, but by the same token a truly applied load and a precision measurement therefore become significant criteria. One preferred testing machine for use with the test apparatus of the present invention is Model 858 manufactured by MTS of Eden Prairie, Minn. Note the mounting of the test fixture into the load-producing machine may be made in any manner appropriate to the machine itself. Typically, each of the outer test-fixture plates will form openings through which a coupling device may be attached. Any suitable load may be applied along the axis of testing.

A strain gauge or extensometer may be present in the load-producing machine itself or may be attached to the test fixture using an appropriate support. Where testing to fatigue failure is to be performed, a counter will also be required. This counter may count actual load applications or may simply record the elapsed time from start to failure of repetitive loads that are being applied at a known rate.

Failure, of course, may be defined as deformation beyond a pre-determined threshold, or as complete failure, for example cracking or separation of the component from its mounting. In some instances, it may also be desirable to establish certain electrical connections to and from the component being tested, with failure being defined as the inability to perform a particular function or functions.

Test Fixture—In General

Figure 3:
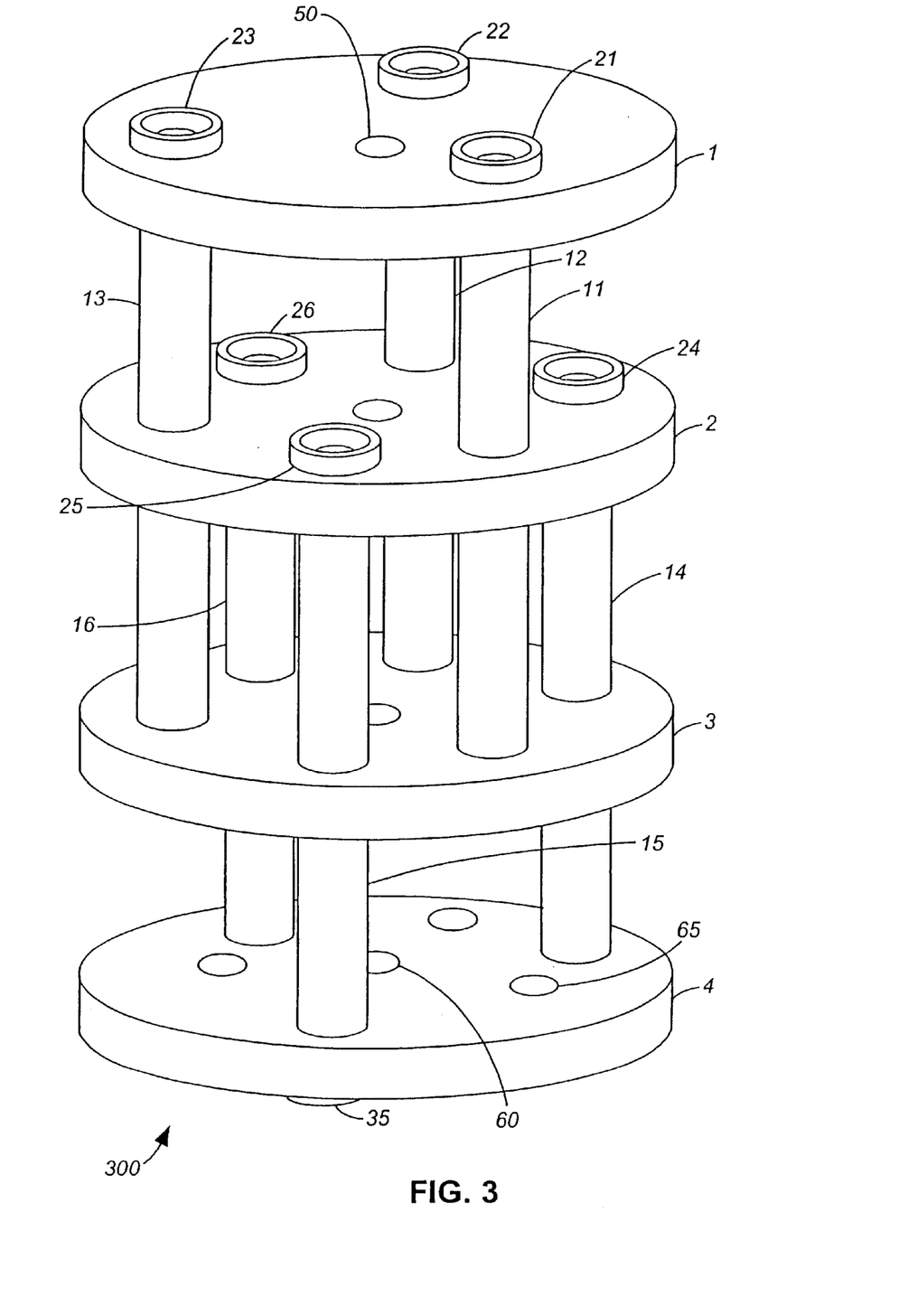
FIG. 3 is an illustration of the basic test fixture according to an embodiment of the present invention.

FIG. 3 is an isometric view of a basic test fixture according to an embodiment of the present invention. The term "basic" will herein be used to generally describe the apparatus without the loading arms installed. Note that in this embodiment, both tensile and shear testing is accomplished by a load-testing machine that applies a tensile force. As will be apparent, to one skilled in the art, however, a compression tester could be used as well, with the apparartus described below modified accordingly.

In a preferred embodiment, the test fixture 300 includes four plates, here denominated 1, 2, 3, and 4, the plates being numbered in order beginning at the top of FIG. 3. Note that this "top" is arbitrary, and although the relationship between the plates will be seen to have some importance, their orientation will not. Plates 1–4 are, as illustrated, preferably uniform and round in shape, with the center typically being defined by the axis of testing-force application. Each plate has a thickness along this axis, and the thickness of each plate in the fixture is preferably, though not necessarily, the same. Although the individual plates differ somewhat in their function, they may be machined so as to be interchangeable from one position to the other (though not so depicted in FIG. 3).

Figure 12:
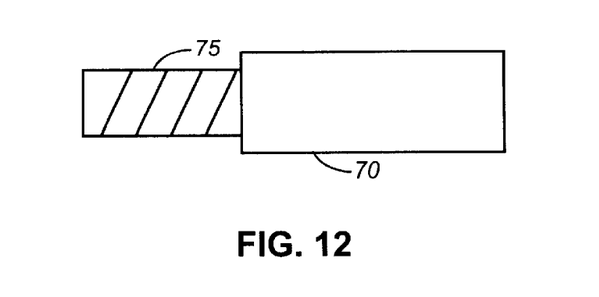
FIG. 12 is an illustration of an extensometer support of use with the test fixture according to an embodiment of the present invention.

The preferred embodiment of the test fixture of the present invention further includes six rods, enumerated in FIG. 3 as rod 11, rod 12, rod 13, rod 14, rod 15, and rod 16. Each rod has a top end and a bottom end, again denominated for convenience by their orientation in FIG. 3, although again the test fixture may be used in any orientation. At their top end, rod 11, rod 12, and rod 13 are fixed to plate 1. "Fixed", as used herein, means prevented from moving in the direction relevant to the test being performed and the test machine used. For example, the rods fixed to plate 1 may simply be attached by threaded connection. Or they may extend through the top of plate 1 and secured by threaded rings 21–23 as shown in FIG. 3. Threaded rings 21–23 prevent plate 1 from being raised above the rods, but do not restrict its downward movement along them. Such a restriction is unnecessary, however, when the fixture as shown is mounted in a tensile-load machine. Plate 1 forms opening 50 through which it is attached to the testing machine, preferably using a threaded connection or some other equivalent means. Plate 4 (like plate 1) forms a threaded opening 60 for attaching to the force-producing machine. Rings 24–26 fix alignment rods 14–16, respectively, to plate 2. The bottoms of the alignment rods are similarly secured, for example by ring 35 visible in FIG. 3. Again, as "fixed" in the embodiment of FIG. 3, plates 1 and 2 are nevertheless free to slide downward, and plates 3 and 4 to move in the opposite direction. Of course, other types of connection are also possible, such as one where all or some of the rod-plate connections permit no such relative movement. If the test fixture is used in connection with a compression testing machine, of course, the rods and plates would have to be fixed in at least the opposite direction.

Note, however, that if not fixed in the downward direction, plate 2 must be held apart from plate 3 (that is, not allowed to impart an impact upon the specimen until such time as testing commences. Again, fixture 300 may be used in any orientation and if the test fixture is horizontal, for example, such restraint would not be necessary. Plate 4 also forms one or more openings, such as opening 65, through which measurement equipment such as extensometer support 70 (shown in FIG. 12) may be inserted for mounting. Of course, such openings may be present in the other plates as well, and the openings may be threaded so as to retain the mounted equipment.

In general, the basic test fixture 300, as shown in FIG. 3, includes two outer plates and two inner plates, which are essentially stacked in a spaced relationship. A plurality of alignment rods (preferably three) connect one outer plate and one inner plate, passing through openings formed in the other inner plate. This other inner plate and the second outer plate are connected in the same fashion. This configuration is preferred because it transmits a force applied to the outer plates to the inner plates while preventing (to a great extent) the direction of force application from moving off-axis. It will be apparent that application of an external force causing the outer plates to move in one direction with respect to each other will cause the inner plate to the opposite tendency. In other words, pulling the outer plates apart will bring the inner plates toward each other, and vice versa. This allows the basic test fixture to be fitted for either pull or shear testing in a machine that applies a compressive or tensile force. It also provides the ability to perform the same type of destructive testing on a number of like components, but using different plates of the test-fixture, perhaps to compare the results for calibration or establishing a baseline.

With regard to the components of the basic test fixture 300, it should be noted that the shape and uniformity of components illustrated in FIG. 3 is preferred, but not required. There is no requirement, for example, that the plates or rods be round when viewed along the testing axis, or that they all be the same size, either in thickness or surface area. Nor is there a requirement that any component be symmetrical about one or more axes. A single plate could even vary in thickness, although in that case the varying thickness would be accounted for when the alignment rods are attached.

In some applications, an additional space plate or plates (not shown) may be used. Usually positioned outside one or both outer places, the spacer plates form openings to receive ports that extend beyond the outer plate, such as the end of an alignment rod or the threaded ring retaining it (See, e.g., FIG. 3). In this way, the test fixture offers a regular; relatively large, flat surface to the testing machine. In machines such as the MTS 850, which include a table for setting the test fixture on, this is preferred to simply supporting the test fixture on the protruding ends of the alignment rods. The spacer plates are optional, but if present may be formed to fit the particular test fixture and test machine being used. The spacer plate or plates may or may not be attached to the test fixture or help retain it in place. Where desired, a jig for attaching the fixture may also be included.

The test fixture 300 fitted for shear and for pull testing will now be described.

Shear Test Fixture

Figure 4:
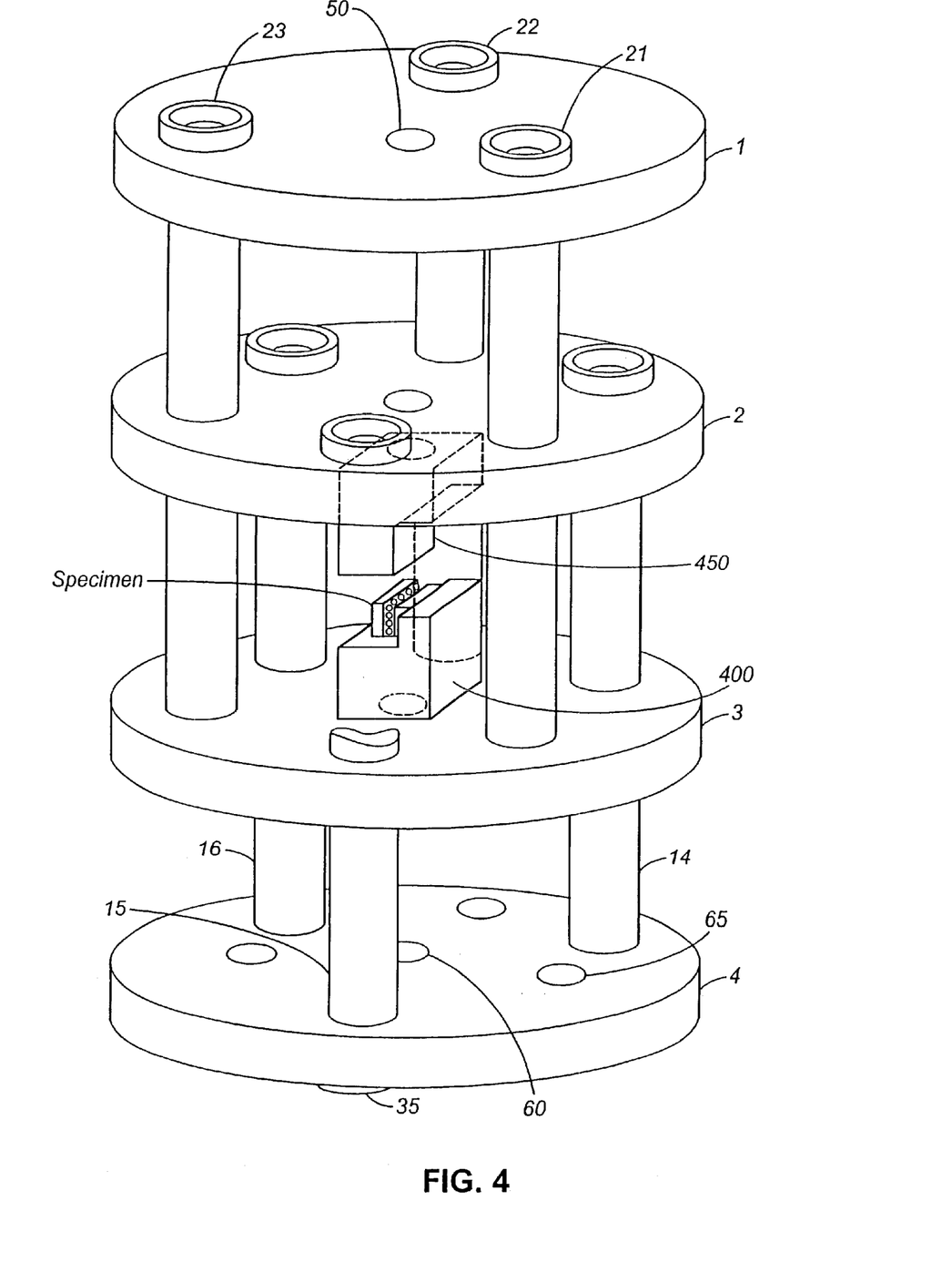
FIG. 4 is an illustration of the test fixture of FIG. 3 with loading arms installed for shear testing according to an embodiment of the present invention.

FIG. 4 is an isometric view of test fixture 300, fitted for shear testing according to one embodiment of the present invention. (Note that rod 15 has been cut away in this view.) The purpose of the shear test fixture is to avoid misalignment and provide shear force to the mounted electronic component that is as true as practicable. In this embodiment, the loading arms 400 and 450 are attached to plate 2 and plate 3, that is, positioned between the two inner plates. As should be apparent, this configuration is suitable for applying a shear force to the specimen as the outer plates are pulled apart. Again, the convention of calling out an upper and lower component based on the orientation in the drawing will be used, even though the fixture may be used in other orientations as well. Using this convention, the lower loading arm 400 is fixed to plate 3 and the upper loading arm 450 is fixed to plate 2. Note that the upper arm 450 and lower arm 400 are shown in only simple configuration to illustrate how they are attached to the basic test fixture 300. (A more detailed view of the arms is given in FIGS. 5–8).

The loading arms may be attached to their respective plates by any suitable means. Note that as used herein "fixed" or "attached" means only that the loading arm is held in place as is necessary and desirable under the circumstances. In some instances, no actual attachment at all is required, the specimen-bearing loading arms simply being disposed between two converging plates being sufficient for whatever testing is being done. In one embodiment (not shown), the face of a test-fixture plate may form a recess for receiving a loading arm, thereby preventing lateral movement. This may be a useful feature regardless of whether or what type of fastener is used to secure the loading arm to the plate.

The loading arms (either or both of them) may be secured to the plates either before or after the specimen is inserted. The specimen is preferably attached using an adhesive to the inner face of the lower loading arm 400. A shear-testing attachment (see FIG. 6) is attached to the upper arm, and aligned to contact the specimen appropriately. Once mounted in this fashion, shear testing may be conducted.

Figure 5A:
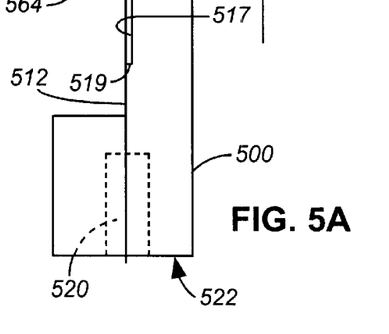
FIG. 5A, a side view of the lower loading arm.
Figure 5B:
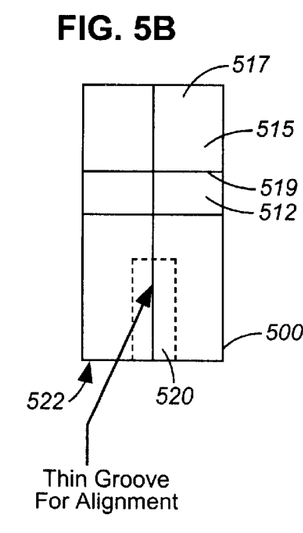
FIG. 5B, a front view of the lower loading arm.
Figure 5C:
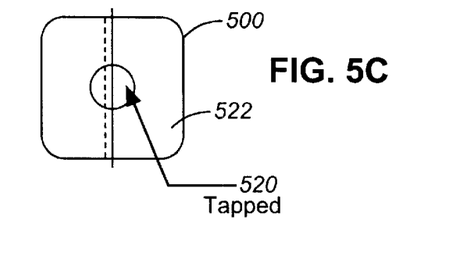
FIG. 5C, a bottom view of the lower loading arm.
Figure 5D:
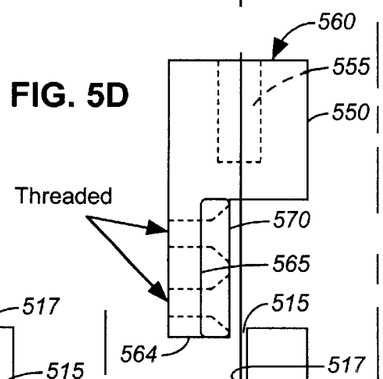
FIG. 5D, a side view of the top loading arm.
Figure 5E:
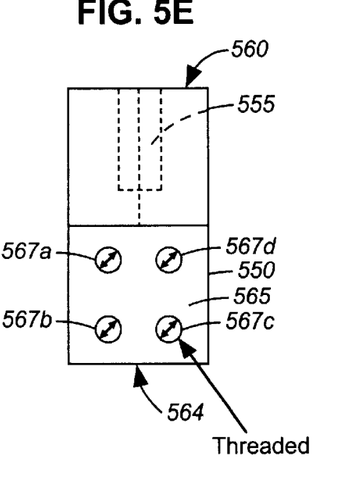
FIG. 5E, a front view of the top loading arm.
Figure 5F:
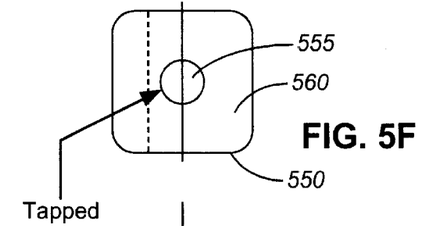
FIG. 5F, a top view of the top loading arm.

FIG. 5 is a detailed illustration of loading arms used for shear testing according to one embodiment of the present invention, and includes FIG. 5A, a side view of the lower loading arm 500; FIG. 5B, a front view of the lower loading arm 500; FIG. 5C, a bottom view of the lower loading arm 500; FIG. 5D, a side view of the top loading arm 550; FIG. 5E, a front view of the top loading arm 550; and FIG. 5F, a top view of the top loading arm 550. The specimen (not shown) is preferably affixed to the back wall 517 of recess 515 of inner face 512 of lower arm 500 using some form of adhesive. The most reliable results will be obtained if the specimen is mounted flat against back wall 517 and edge 519 of recess 515. A threaded recess 520 is tapped into bottom face 522 of lower arm 500 for receiving a threaded bolt or other fastener (not shown) to secure lower arm 500 to the appropriate test-fixture plate (generally plate—see FIG. 4). As mentioned above, any other suitable means for attaching to the test-fixture plate may also be used, with the plate and lower arm 500 modified appropriately.

Upper loading arm 550 includes a threaded recess 555 in top face 560 for the purpose of receiving a threaded bolt or other fastener used to attach upper loading arm 550 to a test-fixture plate. End 564 of inner face 565 may be the structure that actually applies the shear force to the specimen, but preferably attachment 570 is present for this purpose. As more clearly seen in FIG. 5E, a front view of shear-loading arm 550, a plurality of threaded openings, here 567a–d, are formed to receive the fasteners (not shown) by which attachment 570 (shown in FIGS. 5D and 6) is affixed. The use of attachment 570 may alleviate the need to machine upper loading arm 550 to exact tolerances. In an alternate embodiment, attachment 570 is adjustably mountable onto shear-loading arm 550 so that fine adjustments can be made once the loading arms and specimen are in place.

Figure 6:
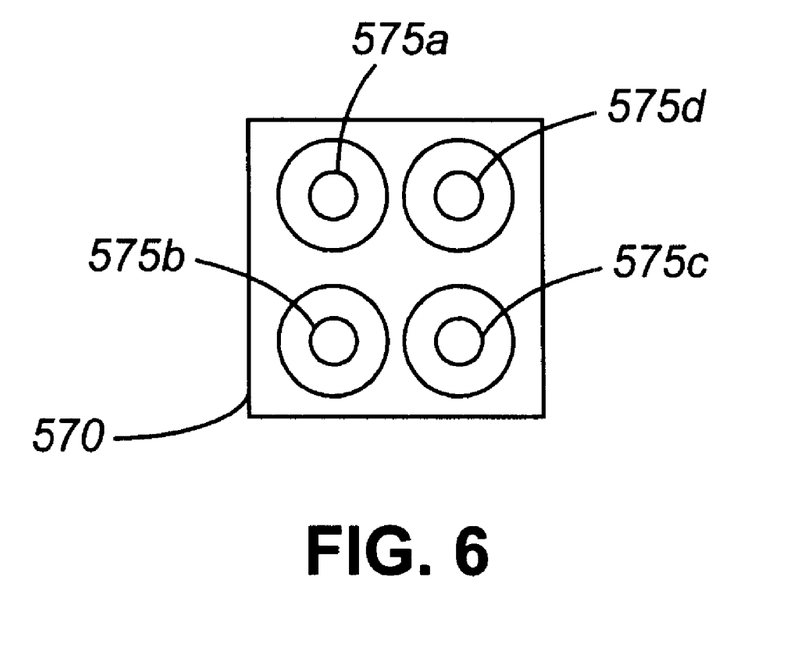
FIG. 6 is a front view of the shear-testing attachment of FIG. 5D.

FIG. 6 is a front view of the shear-loading attachment 570 for upper shear loading arm 550 (shown in FIG. 5). In a preferred embodiment, openings 575a–d are tapered for receiving flathead socket screws or similar fasteners for attaching shear-loading attachment 570 of upper shear loading arm 550. In an alternate embodiment (not shown), the fastener openings formed in shear loading attachment are slotted such that its position is adjustable. In yet another embodiment, threaded fastener openings permit positioning attachment 570 in a spaced-apart relationship to face 565, or a shim (not shown) could be installed between shear-loading attachment 570 and face 565 to accomplish the same result.

Figures 7A, 7C:
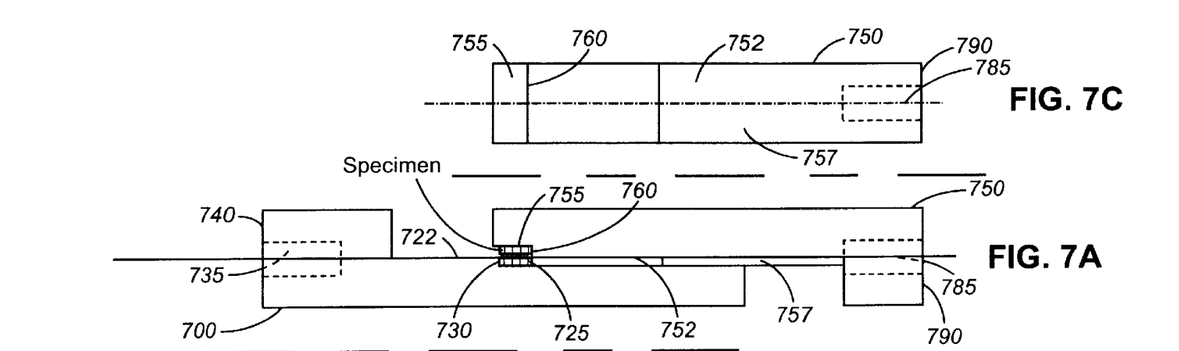
Figures 7B, 7D:
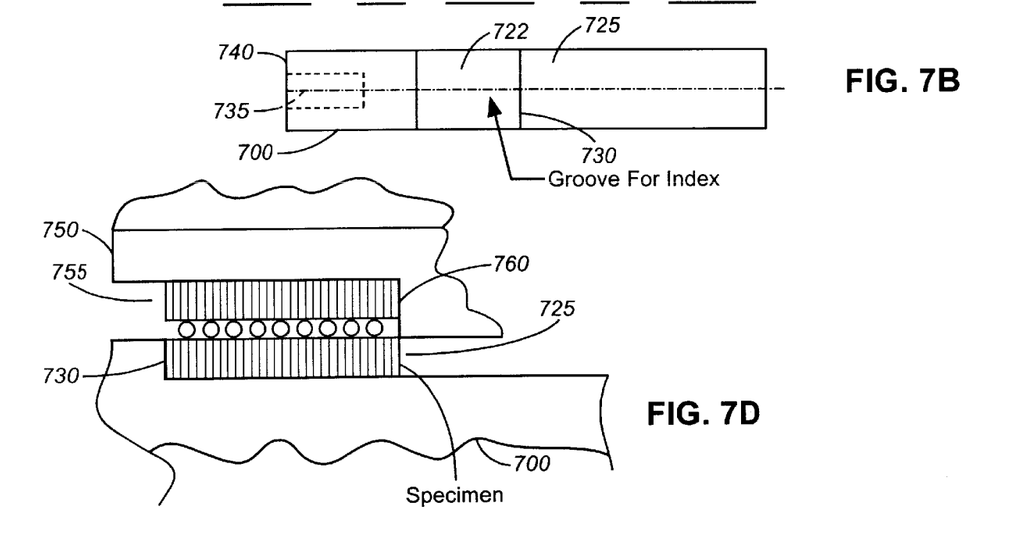
FIG. 7B, a front view of the lower loading arm.
FIG. 7D, a partial close-up side view of upper arm and lower arm capturing a specimen for shear testing.

FIG. 7 is a detailed illustration of the test-fixture shear-test loading arms according to an alternate embodiment of the present invention, and includes FIG. 7A, a side view of both arms in testing position; FIG. 7B, a front view of the lower loading arm 700; FIG. 7C, a front view of the upper loading arm 750; and FIG. 7D, a partial close-up side view of upper arm 750 and lower arm 700 capturing a specimen for shear testing. Note that this embodiment will be described with the test fixture in a horizontal orientation as compared to FIG. 4, although again, no particular orientation is required. In the embodiment of FIG. 7, the specimen is 'captured' between upper loading arm 750 and lower loading arm 700. This configuration helps to prevent the turning or twisting of the specimen as the load is applied. Additional prevention of this undesirable deformation may be obtained by a collar or clamp (not shown) to capture upper loading arm 750 and lower loading arm 700 at the location along there length where the sample is being held.

Returning to the embodiment of FIG. 7, upper loading arm 750 preferably features a recess 755 having an edge 760 formed on inner face 752. Correspondingly, lower loading arm 700 has an inner face 722 forming recess 725 having an edge 730. The specimen is received in recesses 725 and 755, and the shear force is applied by edges 730 and 760. The inner face 752 of upper loading arm 750 also forms step extension 757 to maintain a spaced relationship to the inner face 722 of lower arm 700 so that edge 760 contacts only the upper portion, not all of the specimen. Step extension 757 is only one means for maintaining this spaced relationship, and may not be required at all if satisfactory spacing is otherwise obtained. In an alternate embodiment (not shown) the spacing relationship is maintained by an adjustable structure so that the size of the space may be varied. This same result may be obtained by using shims of varying size. Threaded recesses 735 and 785, formed in bottom face 740 of lower loading arm 700 and bottom face 790 of upper loading arm 750, respectively, are preferably present in order to facilitate attachment to the appropriate test-fixture plates. Of course, other methods of fixing the loading arms to test-fixture plates may be used as well. Note also that the various features of the loading arms may change in size relative to each other, which may be necessary to accommodate different sizes and shapes of specimens.

Figures 8A, 8B, 8C, 8D, 8E:
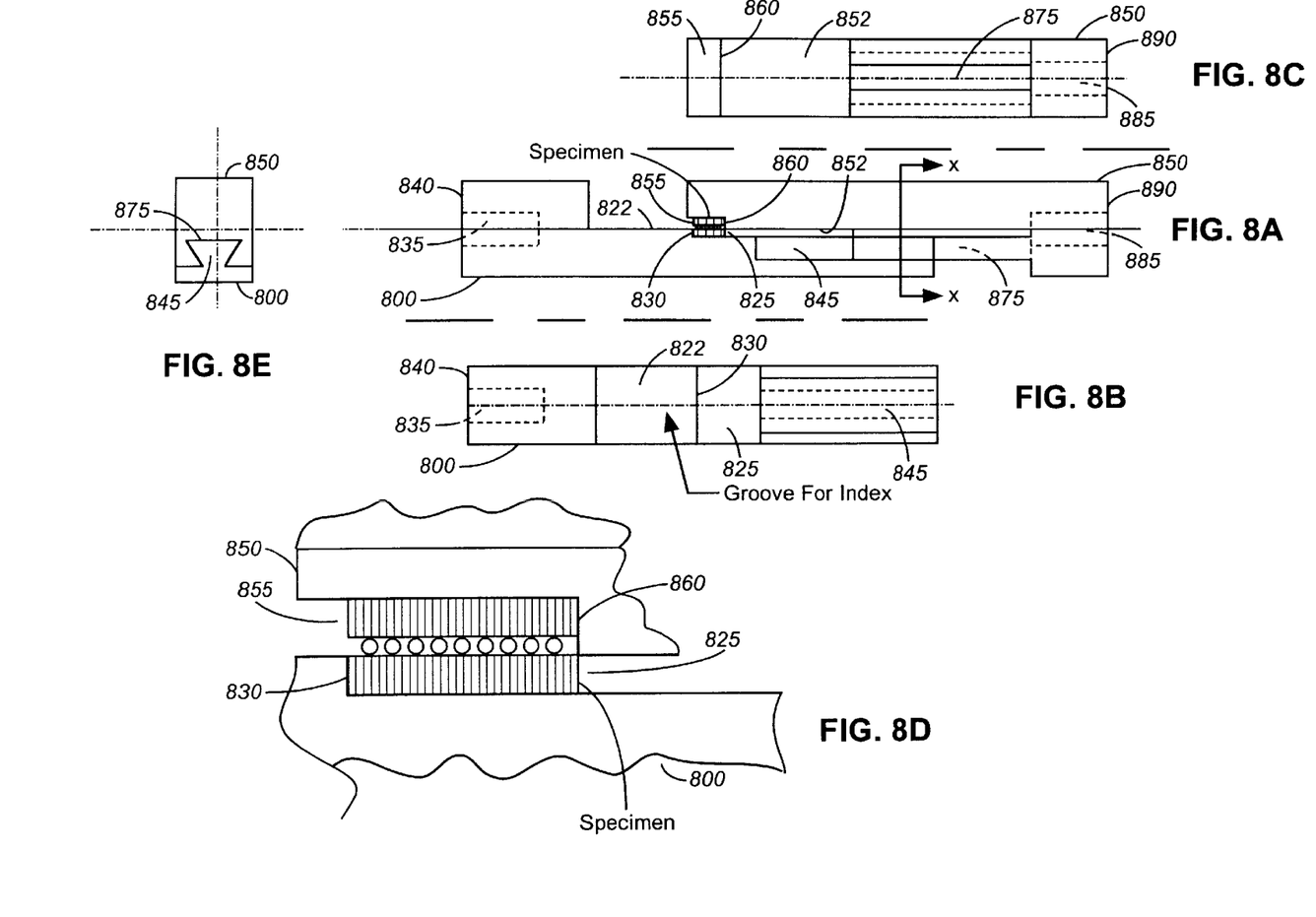

FIG. 8 is a detailed illustration of the test-fixture shear-test loading arms according to an alternate embodiment of the present invention, and includes FIG. 8A, a side view of both arms in testing position; FIG. 8B, a front view of the lower loading arm 800; FIG. 8C, a front view of the upper loading arm 850; FIG. 8D, a partial close-up side view of upper arm 850 and lower arm 800 capturing a specimen for shear testing; and FIG. 8E, a sectional view illustrating the dove-tail and groove, taken along line X—X shown in FIG. 8A. Note that this embodiment is similar to the embodiment of FIG. 7 except that the step extension 757 is replaced by a dove-tail and groove joint. This configuration further helps to prevent application-force misalignment, and is particularly advantageous where varying orientation of the test fixture is required. Similar to the embodiment of FIG. 7, in the embodiment of FIG. 8 the specimen is 'captured' between upper loading arm 850 and lower loading arm 800 to prevent undesirable deformation of the specimen as the load is applied. Preferably, upper loading arm 850 features a recess 855 having an edge 860 formed on inner face 852. Correspondingly, lower loading arm 800 has an inner face 822 forming recess 825 having an edge 830. The specimen is received in recesses 825 and 855, and the shear force is applied by edges 830 and 860. The inner face 852 of upper loading arm 850 also forms step extension 857 to maintain a spaced relationship to the inner face 822 of lower arm 800 so that edge 860 contacts only the upper portion, not all of the specimen. Threaded recesses 835 and 885, formed in bottom face 840 of lower loading arm 800 and bottom face 890 of upper loading arm 850, respectively, are preferably present in order to facilitate attachment to the appropriate test-fixture plates.

In the embodiment of FIG. 8, a dove-tail and groove cooperative structure is used to maintain the relative position of the loading arms before and during testing. Here, lower loading arm 800 forms a dove-tail that is received in groove 875 that is formed in upper loading arm 850. As will be apparent to one skilled in the art, these features may be reversed, that is, the dove-tail structure may alternately be formed by upper loading arm 850. In addition, the precise shape of the dove-tail and groove is unimportant, so long as the two features are able to properly cooperate with each other. And as with the step extension 757 shown in FIG. 7, the dove-tail and groove may be appropriately modified so as to be adjustable so that the spacing between upper arm 850 and lower arm 800 can be varied to accommodate differently sized specimens.

Pull Test Fixture

Figure 9:
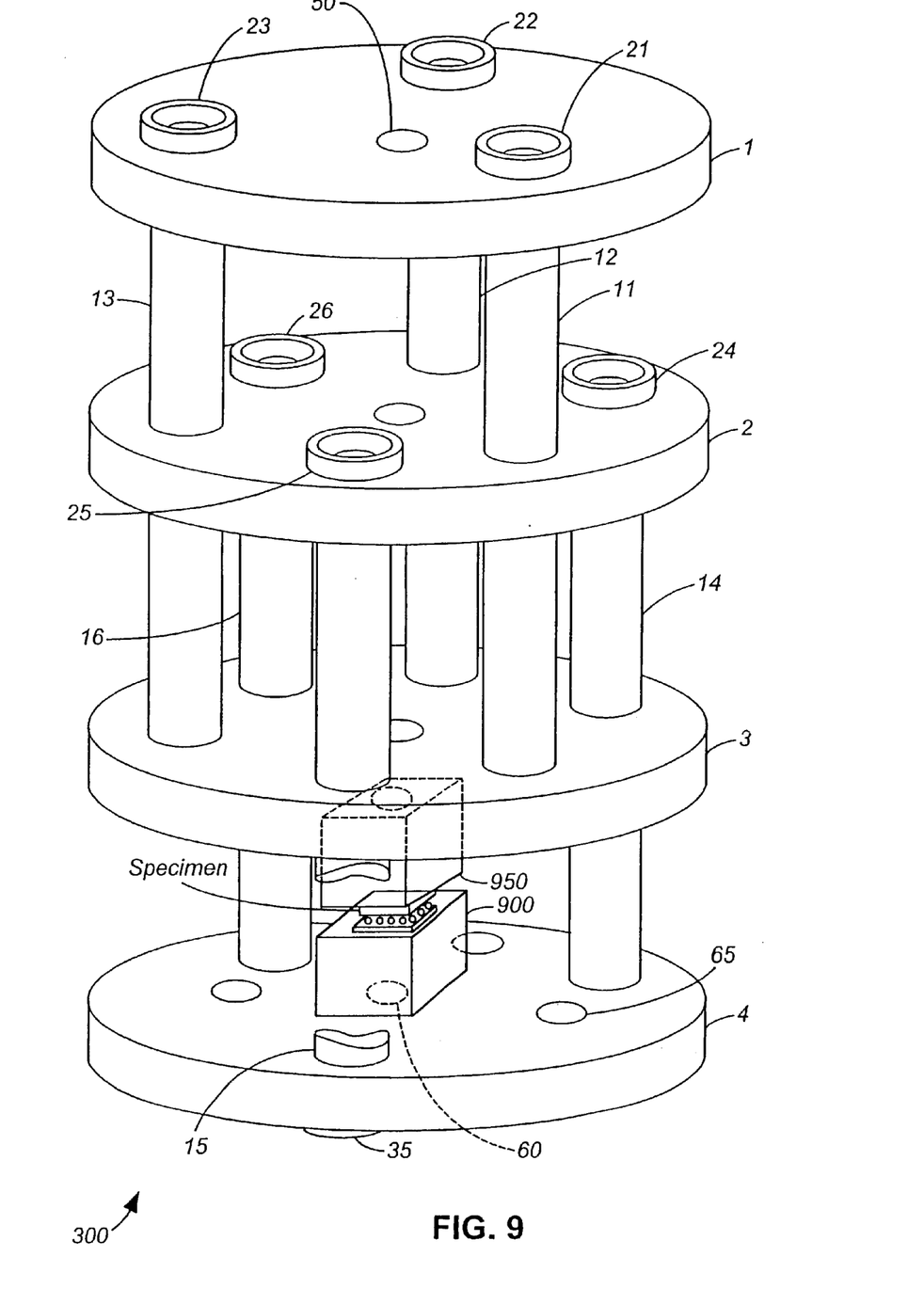
FIG. 9 is an illustration of the test fixture of FIG. 3 with loading arms installed for pull testing according to an embodiment of the present invention.

FIG. 9 is an isometric view of a test fixture, fitted for pull testing according to one embodiment of the present invention. (Again, alignment rod 15 is shown cut-away.) Pull testing simply measures the tensile strength of the specimen, here again a ball-grid array (BGA) chip mounted on a (portion of a) printed circuit board (PCB). In the illustrated embodiment lower loading arm 900 is fixed to plate 4 of test fixture 300, and upper loading arm 950 is fixed to plate 3. Again, this configuration is used because test fixture 300 is assumed to be for use in a machine that applies a tensile force to plates 1 and 4, which will tend to cause plates 3 and 4 to move apart as well. As mentioned previously, this configuration is preferred but not required. The specimen for this test must of course be attached, preferably with an adhesive, to both upper loading arm 950 and lower loading arm 900. The remaining components of test fixture 300 shown in FIG. 9 are numbered, but have already been described in reference to FIG. 3.

Figures 10A, 10B, 10C:
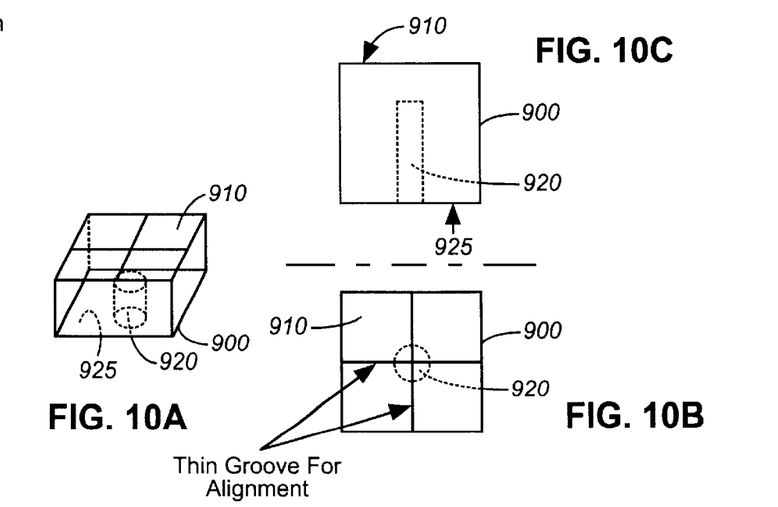
Figure 10D:
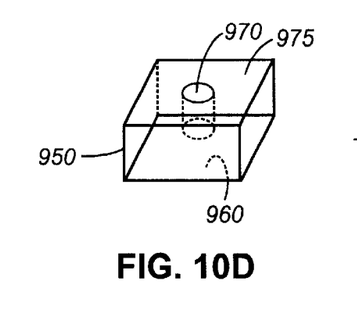
FIG. 10D, an isometric view of the upper loading arm.
Figure 10E:
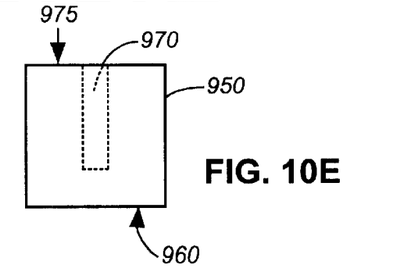
FIG. 10E, a top view of the upper loading arm.
Figure 10F:
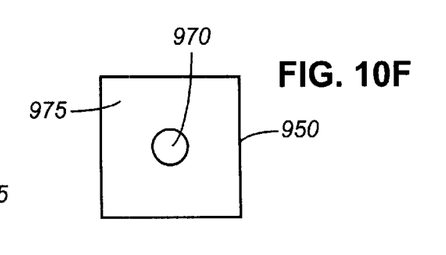
FIG. 10F, a side view of the upper loading arm.

FIG. 10 is a detailed illustration of the loading arms for pull testing according to an embodiment of the present invention and includes FIG. 10A, an isometric view of the lower loading arm 900; FIG. 10B, a top view of the lower loading arm 900; FIG. 10C, a side view of the lower loading arm 900; FIG. 10D, an isometric view of the upper loading arm 950; FIG. 10E, a top view of the upper loading arm 950; and FIG. 10F, a side view of the upper loading arm 950. As shown in FIGS. 10A–10C, lower loading arm 900 forms a threaded recess 920 in bottom face 925 to receive a threaded fastener (not shown) for attachment to plate 4 of test fixture 300. As pointed out in FIG. 10B, inner face 910 of lower loading arm 900 may form thin grooves for alignment. FIGS. 10C–10E similarly show upper loading arm 950 having a threaded recess 970 formed in top face 975. The inner face 960 of upper loading arm will be attached to the specimen (not shown) loaded for testing.

With regard to the pull test fixture of FIGS. 9 and 10, note that although upper loading arm 950 and lower loading arm 900 are shown as uniform in size, this is not a requirement of the present invention, nor is the illustrated shape of the loading arms. In an alternate embodiment (not shown), after a specimen is mounted the loading arms may be captured in a device that constrains their movement in any direction except along the axis of testing. This device may include one or more structures along with the loading arms may travel during pull testing, or may constitute an actual open-ended enclosure. Such an addition to the illustrated embodiment would further help to prevent misalignment of the applied testing force, and also help to prevent lateral movement or rotation of the loading arms.

Figure 11:
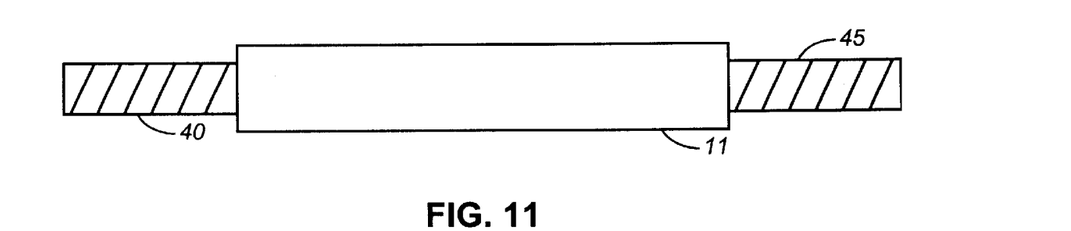
FIG. 11 is an illustration of an exemplary alignment rod for use with the test fixture according to one embodiment of the present invention.

FIG. 11 is an illustration of an exemplary alignment rod 11 for use with the test fixture 300 according to one embodiment of the present invention. Alignment rod 11, which again may take on any suitable shape, includes threaded upper end 40 and threaded lower end 45 for using in fixing it to plates 1 and 3 (See FIG. 3). Note that, although shown the same, end 40 and end 45 of alignment rod 11 could be different as well.

FIG. 12 is an illustration of an extensometer support 70 of use with the test fixture 300 according to an embodiment of the present invention. Extensometer support 70 is one of several equipment attachments that can be used to measure stress and strain during testing conducted using test fixture 300 (appropriately equipped with loading arms). Threaded end 75 of extensometer support 70 provides an exemplary means for attachment to one of the test-fixture plates.

Finally, note that the description above provides exemplary and preferred embodiments for implementing the present invention. The scope of the invention, however, should not necessarily be limited by this description. The scope of the present invention is defined by the claims set forth below. In particular, note that the reference numbers used in the description above are not intended to correlate exactly with the designation of a "first" or "second" component or feature in the claims.

What is claimed is:

1. A test fixture for the destructive testing of a mounted electrical component by applying a load along a testing axis, said test fixture comprising:
   a first plate oriented normally to the testing axis;
   a first plurality of alignment rods fixed to the first plate, each of the plurality of alignment rods having a longitudinal dimension oriented parallel to the testing axis;
   a second plate oriented normally to the testing axis and fixed to the first plurality of alignment rods, such that a first force applied to the first plate along the testing axis is transmitted to the second plate through the first plurality of rods;
   a third plate oriented normally to the testing axis and disposed in a spaced relationship between the first plate and the second plate, the third plate forming a plurality of openings such that the first plurality of alignment rods may pass therethrough;

a second plurality of alignment rods fixed to the third plate, each of the plurality of rods having a longitudinal dimension oriented parallel to the testing axis, wherein the second plate forms a plurality of openings such that the second plurality of alignment rods may pass therethrough;

a fourth plate oriented normally to the testing axis, such that the second plate is disposed in a spaced relationship between the third plate and the fourth plate, the fourth plate fixed to the second plurality of rods such that a second force applied to the fourth plate along the testing axis is transmitted to the third plate through the second plurality of rods;

a specimen holder comprising at least two loading arms, the at least two loading arms being fixed to any selected adjacent pair of the first, second, third, or fourth plates, to position the loading arms in opposition with one another, specimen holder for holding the mounted electrical component, the first force and the second force applied to the first plate and to the fourth place opposing one another and imparted to the mounted electrical component by way of the selected adjacent pair of the plates and the loading arms of the specimen holder.

2. The test fixture of claim 1, wherein the first plurality of alignment rods comprises three rods.

3. The test fixture of claim 1, wherein the second plurality of alignment rods comprises three rods.

4. The test fixture of claim 1, wherein the respective plates and rods are fixed such that the first force and the second force comprise a testing load applied to the mounted electrical component, the first and second forces, respectively, applied in directions along the testing axis tending to force the first plate and the fourth plate away from each other.

5. The test fixture of claim 1, wherein the respective plates and rods are fixed such that the first force and the second force comprise a testing load applied to the mounted electrical component, the first and second forces, respectively, applied in directions along the testing axis tending to force the first plate and the fourth plate toward each other.

6. The test fixture of claim 1, wherein a first of the at least two loading arms is fixed to the second plate.

7. The test fixture of claim 6, wherein a second of the at least two loading arms is fixed to the third plate.

8. The test fixture of claim 6, wherein a second of the at least two loading arms is fixed to the fourth plate.

9. The test fixture of claim 1, wherein the mounted electrical component is fixed to at least one of the loading arms by an adhesive.

10. The test fixture of claim 1, wherein the two loading arms comprising the specimen holder are positioned so as to contact each other.

11. The test fixture of claim 10, wherein the two loading arms a dove-tail and groove joint and wherein the two loading arms contact each other at the dove-tail and groove joint.

12. A method for testing a mounted electronic component, said method comprising the steps of:

affixing the mounted electronic a component to a first loading arm;

fixing the first loading arm to a first test-fixture plate of a test fixture, wherein the first test-fixture plate is connected to a second text-fixture plate by a first plurality of alignment rods;

fixing a second loading arm to a third test-fixture plate such that the second loading arm is adjacent to the mounted electronic component, wherein the third test fixture plate is connected to a fourth test-fixture plate by a second plurality of alignment rods; and, applying a first force to the second test-fixture plate and a second force to the fourth test-fixture plate, the first force tending to move the second test-fixture plate relative to the fourth test-fixture plate and the second force tending to move the fourth test-fixture plate relative to the second test-fixture plate, thereby causing a load to be applied to the component.

13. The method of claim 12, wherein the mounted electronic component is affixed to the first loading arm using an adhesive.

14. The method of claim 12, further comprising the step of affixing the mounted electronic component to the second loading arm prior to applying the first and second testing forces, respectively.

15. The method of claim 14, wherein the step of applying the first and second forces results in a tensile force tending to pull the component from the structure to which it is mounted.

16. The method of claim 12, wherein the step of applying a force results in a shear force being applied to the mounted electronic component.

17. The method of claim 16, wherein the mounted electronic component is affixed to the second testing arm.

* * * * *